(12) United States Patent
Zink et al.

(10) Patent No.: US 6,384,284 B1
(45) Date of Patent: May 7, 2002

(54) BIPHENYL COMPOUNDS SUBSTITUTED BY CAMPHOR OR HYDANTOIN DERIVATIVES AS SUNSCREEN COMPOSITIONS

(75) Inventors: Rudolf Zink, Therwil (CH); Dieter Reinehr, Kandern (DE); Helmut Luther; Bernd Herzog, both of Grenzach-Wyhlen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/806,358

(22) PCT Filed: Sep. 21, 1999

(86) PCT No.: PCT/EP99/06985

§ 371 Date: Mar. 29, 2001

§ 102(e) Date: Mar. 29, 2001

(87) PCT Pub. No.: WO00/20384

PCT Pub. Date: Apr. 13, 2000

(30) Foreign Application Priority Data

Oct. 2, 1998 (EP) ............................................. 98810992

(51) Int. Cl.⁷ ...................... C07C 49/00; C07D 235/00; C07D 235/02; A61K 7/42; A61K 7/44
(52) U.S. Cl. ...................... 568/313; 568/318; 568/326; 568/330; 568/333; 568/339; 548/301.7; 548/312.1; 424/59; 424/60
(58) Field of Search .................................. 568/313, 318, 568/326, 330, 333, 339; 548/301.7, 312.1; 424/59, 60

(56) References Cited

U.S. PATENT DOCUMENTS

| | | | |
|---|---|---|---|
| 4,797,493 A | 1/1989 | Matsuno et al. | 548/312 |
| 5,064,641 A | 11/1991 | Lang et al. | 424/60 |
| 5,677,314 A | 10/1997 | Stein et al. | 514/305 |
| 5,730,960 A | 3/1998 | Stein et al. | 424/59 |

FOREIGN PATENT DOCUMENTS

| | | |
|---|---|---|
| DE | 2415819 | 10/1975 |
| DE | 3713094 | 10/1987 |
| DE | 4442324 | 5/1996 |
| EP | 0370867 | 5/1990 |
| EP | 0693471 | 1/1996 |

*Primary Examiner*—Johann Richter
*Assistant Examiner*—Sikarl A. Witherspoon
(74) *Attorney, Agent, or Firm*—Kevin T. Mansfield

(57) ABSTRACT

A description is given of diphenyl compounds of formula

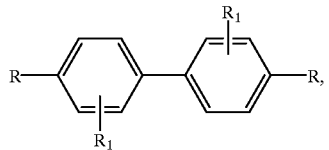

(1)

wherein
  R is a camphor or hydantoin derivative; and
  $R_1$ is hydrogen; or $C_1$–$C_5$ alkyl.
These compounds are suitable as light stabilizers in cosmetic, pharmaceutical and veterinary formulations.

7 Claims, No Drawings

BIPHENYL COMPOUNDS SUBSTITUTED BY CAMPHOR OR HYDANTOIN DERIVATIVES AS SUNSCREEN COMPOSITIONS

The present invention relates to diphenyl compounds, to a process for their preparation and to their use as light stabilisers.

Benzylidene camphors and their use as sunscreens in cosmetics are known, for example, from EP-A-0,693,471 and EP-A-0,370,867.

Surprisingly, it has now been found that reaction products of diphenylbisaldehyde and camphor and hydantoin compounds have pronounced photostability.

Accordingly, this invention relates to diphenyl compounds of formula

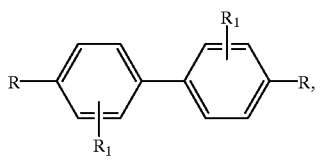

(1)

wherein

R is a camphor or hydantoin derivative; and $R_1$ is hydrogen; or $C_1-C_5$alkyl.

$C_1-C_5$Alkyl is straight-chain or branched alkyl radicals, such as methyl, ethyl, n-propyl, isopropyl, n-butyl, sec-butyl, tert-butyl, amyl, isoamyl or tert-amyl.

Preferred diphenyl compounds are those of formula (1), wherein

R is a radical of formulae

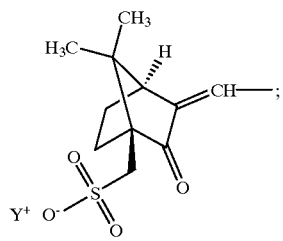

(1a)

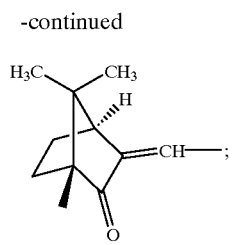

(1b)

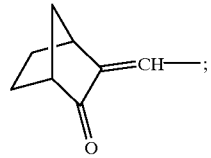

(1c)

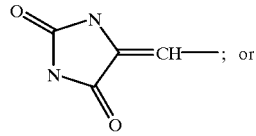

(1d)

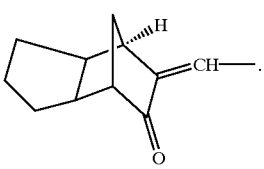

(1e)

In these formulae $Y^+$ is hydrogen; alkali metal; alkaline earth metal, ½ $Zn^{2+}$, ⅓ $Al^{3+}$, ½ $Ba^{2+}$,

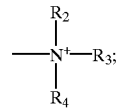

and $R_2$, $R_3$ and $R_4$ are each independently of one another hydrogen; $C_1-C_5$alkyl or hydroxy-$C_1-C_5$alkyl.

Particularly preferred compounds are those of formula

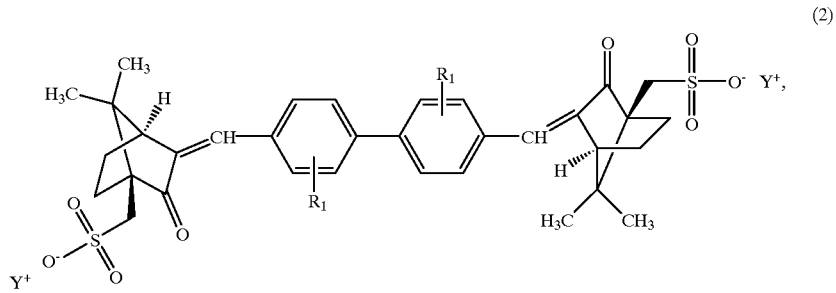

(2)

wherein

R$_1$ is hydrogen; or C$_1$–C$_5$alkyl; and

Y$^+$ has the meaning given in formula (1).

The compounds of formula (1) are obtained, for example, by reacting a diphenylbisaldehyde of formula

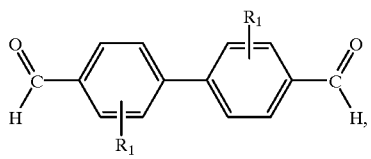

(3)

wherein

R$_1$ has the meaning given in formula (1), in the presence of a base or a Lewis acid with the corresponding camphor or hydantoin derivative.

The reaction is usually carried out in an inert diluent, preferably in a protic solvent, in particular an alcohol, such as methanol, ethanol, isopropanol or tert-butanol, or in an aprotic solvent, such as diethyl ether, toluene or cyclohexane, or in mixtures of the cited solvents.

The base is preferably an alkali alcoholate, such as sodium methylate, sodium ethylate or potassium tert-butylate.

The reaction can be carried out in the temperature range from 0° C. to the boiling point of the reaction mixture, the preferred reaction temperature being in the range from 25 to 60° C.

As a rule, about 0.8 to 1.2 mol of the camphor or hydantoin derivative, based on 1 mol of the compound of formula (1), is used.

The camphor or hydantoin derivatives used as starting compounds are known compounds which are commercially available.

The process for the preparation of the compounds of formula (1) is another subject matter of this invention.

The compounds of formula (1) are particularly suitable as UV filters, i.e. for protecting ultraviolet-sensitive organic materials, especially human and animal skin and hair, from the harmful effect of UV radiation. These compounds are therefore suitable as light stabilisers in cosmetic, pharmaceutical and veterinary formulations. The compounds can be used both in dissolved and in micronised state.

In another of its aspects, this invention relates to a cosmetic formulation comprising a compound of formula (1).

For cosmetic application, these light stabilisers—unless they are water-soluble—usually have an average particle size in the range from 0.02 to 2, preferably from 0.05 to 1.5, particularly preferably from 0.1 to 1.0 nm. The insoluble light stabilisers of this invention can be brought to the desired particle size by conventional methods, for example by grinding using e.g. a nozzle mill, ball mill, vibratory or hammer mill. Grinding is preferably carried out in the presence of 0.1 to 30, preferably of 0.5 to 15% by weight, based on the UV absorber, of a grinding aid, for example a vinyl pyrrolidone polymer, a vinyl pyrrolidone-vinyl acetate copolymer, an acylglutamate, an alkylpolyglucoside or, preferably, a phospholipid.

The light stabilisers can also be used dry in powder form. To this purpose, the light stabilisers are subjected to known grinding processes, such as vacuum atomisation, counter-current spray drying and the like. These powders have a particle size of 0.1 nm to 2 µm. In order to avoid agglomeration processes, the light stabilisers can be coated prior to the pulverisation process with a surfactant, for example with an anionic, nonionic or amphoteric surfactant, e.g. phospholipids or known polymers, such as PVP, acrylates etc.

Besides the novel UV absorber, the cosmetic formulation can also contain one or several UV protectives of the following substance classes.

1. p-Aminobenzoic acid derivatives, such as 4-dimethylaminobenzoic acid-2-ethylhexyl ester;
2. Salicylic acid derivatives, such as salicylic acid-2-ethylhexyl ester;
3. Benzophenone derivatives, such as 2-hydroxy-4-methoxybenzophenone and its 5-sulfonic acid derivative;
4. Dibenzoylmethane derivatives, such as 1-(4-tert-butylphenyl)-3-(4-methoxyphenyl)-propane-1,3-dione;
5. Diphenylacrylates, such as 2-ethylhexyl-2-cyano-3,3-diphenylacrylate and 3-(benzofuranyl)-2-cyanoacrylate;
6. 3-imidazol-4-yl-acrylic acid and 3-imidazol-4-yl-acrylate;
7. Benzofuran derivatives, in particular 2-(p-aminophenyl)benzofuran derivatives, described in EP-A-582,189, U.S. Pat. Nos. 5,338,539, 5,518,713 and EP-A-613,893;
8. Polymeric UV absorbers, such as the benzylidenemalonate derivatives described, inter alia, in EP-A-709,080;
9. Cinnamic acid derivatives, such as the 4-methoxycinnamic acid-2-ethylhexyl ester or isoamyl esters or cinnamic acid derivatives disclosed, inter alia, in U.S. Pat. No. 5,601,811 and WO 97/00851;
10. Camphor derivatives, such as 3-(4'-methyl)benzylidenebornan-2-one, 3-benzylidenebornan-2-one, N-[2(and 4)-2-oxyborn-3-ylidenemethyl)benzyl] acrylamide polymer, 3-(4'-trimethyl ammonium)benzylidenebornan-2-one methylsulfate, 3,3'-(1,4-phenylenedime-thine)bis(7,7-dimethyl-2-oxo-bicyclo-[2.2.1]heptane-1-methanesulfonic acid) and its salts, 3-(4'-sulfo)benzylidenebornan-2-one and its salts;
11. Trianilino-s-triazine derivatives, such as 2,4,6-trianiline-(p-carbo-2'-ethyl-1'-oxi)-1,3,5-triazine and the UV absorbers disclosed in U.S. Pat. No. 5,332,568, EP-A-517,104, EP-A-507,691, WO 93/17002 and EP-A-570,838;
12. 2-Hydroxyphenylbenzotriazole derivatives;
13. 2-Phenylbenzimidazole-5-sulfonic acid and their salts;
14. Menthyl-o-aminobenzoate;
15. Inorganic micropigments, such as TiO$_2$ (differently coated);
16. N-substituted benzimidazoles, such as described in EP-A-0,843,995;
17. Hydroxyphenylbenzotriazoles and their derivatives, in particular siloxane derivatives;
18. Siloxanes of oxanilide derivatives, such as described in EP-A-0,712,856.

It is also possible to use the UV absorbers described in "Sunscreens", Eds. N. J. Lowe, N. A. Shaath, Marcel Dekker, Inc., New York and Basel or in Cosmetics & Toiletries (107), 50ff (1992) as additional UV protectives in the formulation of this invention.

The novel cosmetic formulation can furthermore also be used together with known anti-oxidants, for example amino acids (e.g. glycerol, histidine, tyrosine, tryptophane) and their derivatives, peptides (e.g. carnosine) and their derivatives, vitamin E or vitamin A and their derivatives, derivatives of vitamin C, carotinoids, flavanoids and their derivatives and ubiquinones or HALS (=hindered amine light stabiliser) compounds.

The cosmetic formulations contain 0.1 to 15% by weight, preferably 0.5 to 10% by weight, based on the total weight of the formulation, of a light stabiliser of formula (1) or of a mixture of light stabilisers and a cosmetically compatible auxiliary.

The cosmetic formulations may be prepared by physically mixing the UV absorber(s) with the auxiliary by standard methods, for example by simply stirring the individual components together, preferably by exploiting the solubility characteristics of known cosmetic UV absorbers, such as OMC, isooctyl salicylate and others.

The cosmetic formulations can be formulated as water-in-oil or oil-in-water emulsion, as oil-in-alcohol lotion, as vesicular dispersion of a ionic or nonionic amphiphilic lipid, as gel, solid stick or as aerosol formulation.

As water-in-oil or oil-in-water emulsion, the cosmetically compatible auxiliary preferably comprises 5 to 50% of an oil phase, 5 to 20% of an emulsifier and 30 to 90% of water. The oil phase can in this case contain any oil suitable for cosmetic formulations, for, example one or several hydrocarbon oils, wax, natural oil, silicone oil, fatty acid ester or fatty alcohol. Preferred mono- or polyols are ethanol, isopropanol, propylene glycol, hexylene glycol, glycerol and sorbitol. It is also possible to use di- or/and trivalent metal salts (alkali earth metal, $Al^{3+}$ and others) of one or several alkylcarboxylic acids.

To prepare the cosmetic formulations it is possible to use any conventionally usable emulsifier, typically one or several ethoxylated esters of natural derivatives, such as polyethoxylated esters of hydrogenated castor oil; or silicone oil emulsifiers, such as silicone polyol; free or ethoxylated fatty acid soaps; fatty alcohol or fatty acid and their polyoxethylene derivatives; free or ethoxylated sorbitan esters; ethoxylated fatty acids or fatty acid esters; or ethoxylated glycerides.

Other suitable emulsifiers are partial fatty acid esters of polyvalent alcohols, such as glycol, 1,2-propylene glycol, glycerol, sorbitol and pentaerythritol, and also protein-fatty acid condensates and lanolin derivatives, the salts of alkylcarboxylic acids, alkylsulfates or alkylsulfonates or polyglycol ethers. It is also possible to use mixtures of anionactive and nonionic emulsifiers or mixtures of purely nonionic surface-active substances having different HLB-values. Mixtures of fatty alcohol ethers and fatty acid polyglycol ethers or ethoxylated fats are also conventionally used.

The cosmetic formulations can also contain other components, for example emollients, emulsion stabilisers, skin moisturisers, suntan promoters, thickeners such as xanthan, moisture retention agents such as glycerol, preservatives, fragrances and colourants.

Cosmetic formulations of this invention include different cosmetic compositions. Particularly suitable compositions are, for example, the following:

skin-care products, for example skin washing and cleansing products in the form of bars of soap or liquid soaps, syndets or washing pastes, bath products, for example liquid (foam baths, milks, shower products) or solid bath products, such as bath pearls and bath salts;

skin-care products, such as skin emulsions, multiple emulsions or skin oils;

decorative body-care products, for example face make-ups in the form of day or powder creams, face powders (lose and compressed), rouge or cream make-ups, eye-care products, for example eye shadow products, mascara, eyeliners, eye creams or eye-fix creams; lip-care products, for example lipstick, lip gloss, lip liner; nail-care products, such as nail varnish, nail varnish remover, nail hardeners or cuticle removers;

feminine hygiene products, such as feminine hygiene washing lotions or sprays;

foot-care products, for example foot baths, foot powders, foot creams or foot balms, special deodorants and antiperspirants or products for scrubbing off calluses;

sunscreens, such as sun milks, lotions, creams, oils, sunblockers or tropicals, pre-sun products or after-sun products;

suntanning products, for example self-tanning creams;

depigmenting products, for example products for bleaching or lightening skin;

insect repellents, for example insect oils, lotions, sprays or sticks;

deodorants, for example deodorant sprays, non-aerosol sprays, deodorant gels, sticks or roll-ons;

antiperspirants, for example antiperspirant sticks, creams or roll-ons;

products for cleansing and treating impure skin, for example syndets (solid or liquid), peeling or scrubbing products or peeling masks;

chemical depilatory products, for example depilatory powders, liquid depilatory products, creamy or pasty depilatory products, depilatory gels or aerosol foams;

shaving products, for example shaving soap, foaming shaving creams, non-foaming shaving creams, shaving foams and gels, preshaving products for dry shaving, aftershaves or aftershave lotions;

scents, for example perfumes (Eau de Cologne, Eau de Toilette, Eau de Parfum, Parfum de Toilette, perfume), perfume oils or perfume creams;

products for oral and dental hygiene as well as for dentures, for example toothpastes, tooth gels, tooth powders, mouth-wash concentrates, anti-plaque mouth-washes, denture cleaning products or denture adhesion products;

cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for perms (hot wave, mild wave, cold wave), hair straightening products, liquid hair fixatives, hair foams, hair sprays, bleaching agents, for example hydrogen peroxide solutions, bleaching shampoos, bleaching creams, bleaching powders, bleaching pastes or oils, temporary, semitemporary or permanent hair dyes, products containing self-oxidising dyes, or natural hair dyes, such as henna or camomile.

The formulations listed above can be in different forms of presentation, for example in the form of liquid formulations as W/O, O/W, O/W/O, W/O/W, PIT emulsions and all types of microemulsions, in the form of a gel, in the form of an oil, cream, milk or lotion, in the form of a powder, lacquer, pellets or make-up, in the form of a stick, in the form of a spray (spray with propellant or non-aerosol spray) or an aerosol, in the form of a foam, or in the form of a paste.

The cosmetic formulations are distinguished by excellent protection of the human skin against the harmful effect of sunlight.

In the following Examples, percentages are by weight and amounts used are based on the pure substance.

Working Examples of Novel Compounds

EXAMPLE 1

23.3 g (+−) of camphor-10-sulfonic acid are dissolved in 100 ml of toluene and 5 ml of methanol at 25° C. and are then charged with 11.2 g of sodium methylate and the mixture is heated, with stirring, to 66° C.

A circa 50° C. warm solution consisting of 10.5 g of 1,1′-diphenyl-4,4′-bisaldehyde in 145 ml of toluene and 16 ml of methanol is then added to the above mixture over 2 hours at 66 to 70° C. This temperature is maintained for another 5 hours until no further increase of the product is found in a DC.

Toluene and methanol are then distilled off as an azeotrope while being charged successively with a total of 115 ml of water. A solution forms at 98° C. which is clarified by filtration using some carbon. At about 50° C., 300 ml of methanol are added dropwise and the mixture is cooled to 10° C., the compound crystallising out as a sodium salt. After 2 hours, the precipitate is subjected to filtration and washed with 100 ml of methanol. Drying yields 16.8 g of crude product of the compound of formula

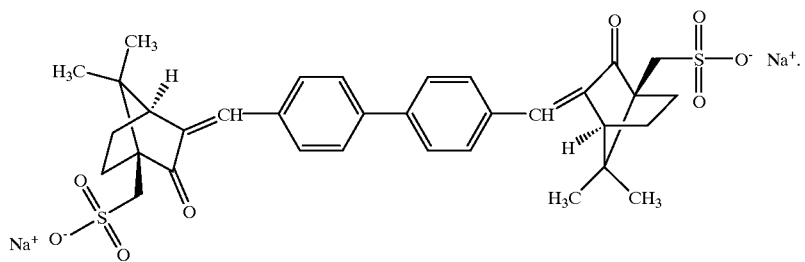

(101)

To purify the crude product, it is dissolved in 150 ml of methanol and 200 ml of water at 50° C. and clarified by filtration. For crystallisation, 200 ml of brine 15% and 100 ml of methanol are added and the mixture is cooled to 10° C. After 2 hours, the precipitate is collected by filtration, washed with 20 ml of methanol/water 1:1 and dried.

A first fraction is obtained which consists of 5.8 g of the pure compound of formula (101). Additional fractions can be obtained from the filtrate.

Elemental analysis (after equilibration in air=6.2% $H_2O$):

|  | C | H | S | O |
|---|---|---|---|---|
| calculated | 56.1 | 5.7 | 8.8 | 23.1 |
| found | 55.5 | 5.7 | 8.4 | 23.6 |

Application Examples

EXAMPLE 2

Preparation of an O/W Lotion

|  | INCI Name | % |
|---|---|---|
| A | polyglyceryl-3 methylglucose distearate | 2.0 |
|  | decyl oleate | 5.7 |
|  | isopropyl palmitate | 5.0 |
|  | caprylic/capric triglyceride | 6.5 |
|  | octyl methoxycinnamate | 5.0 |
| B | glycerol | 3.0 |
|  | phenoxyethanol & (methyl, ethyl, propyl, butyl)parabens | 0.5 |
|  | compound of formula (101) | 2.0 |
|  | deionised water | 60.9 |
| C | carbomer | 0.2 |
|  | isopropyl palmitate | 0.8 |
| D | methylene bis-benzotriazolyl tetrametylbutylphenol (50% suspension) | 8.0 |
| E | NaOH (10%) | as required |

The phases A and B are heated separately to 75–80° C. and are gently combined. This is followed by intense homogenisation and cooling to room temperature with slight stirring. With stirring, D is admixed to the emulsion so obtained and is adjusted to pH 6.5 with E.

An in vitro SPF of 23 is determined by means of an Optometrics SPF-290 analyser (2 $\mu$l/cm$^2$ on Transpore film).

EXAMPLE 3

Preparation of an O/W Emulsion

|  | INCI Name | % |
|---|---|---|
| A | polyglyceryl-3 methylglucose distearate | 2.0 |
|  | decyl oleate | 5.7 |
|  | isopropyl palmitate | 5.0 |
|  | vitamin E acetate | 1.5 |
|  | caprylic/capric triglyceride | 6.5 |
|  | octyl methoxycinnamate | 7.5 |
| B | glycerol | 3.0 |
|  | phenoxyethanol & (methyl, ethyl, propyl, butyl)parabens | 0.5 |
|  | compound of formula (101) | 3.0 |
|  | deionised water | 64.3 |
| C | carbomer | 0.2 |
|  | isopropyl palmitate | 0.8 |
| E | NaOH (10%) | as required |

The phases A and B are heated separately to 75–80° C. and are slowly combined and homogenised. After cooling with slow stirring, the product is adjusted to pH 7.0 with E.

An in vitro SPF of 16 is determined by means of an Optometrics SPF-290 analyser (2 μl/cm² on Transpore film).

EXAMPLE 4

Preparation of an O/W Lotion

| INCI Name | % |
|---|---|
| A polyglyceryl-3 methylglucose distearate | 2.0 |
| decyl oleate | 5.7 |
| isopropyl palmitate | 5.0 |
| caprylic/capric triglyceride | 6.5 |
| bis-octylphenol methoxyphenyl triazine | 3.0 |
| B glycerol | 3.0 |
| phenoxyethanol & (methyl, ethyl, propyl, butyl)parabens | 0.5 |
|  | 2.0 |
| deionised water | 63.3 |
| C carbomer | 0.2 |
| isopropyl palmitate | 0.8 |
| D methylene bis-benzotriazolyl tetrametylbutylphenol (50% suspension) | 8.0 |
| E NaOH (10%) | as required |

The phases A and B are heated separately to 75–80° C. and are gently combined. This is followed by intense homogenisation and cooling to room temperature with slight stirring. With stirring, phase D is admixed to the emulsion so obtained and the mixture is adjusted to pH 6.5 with phase E.

An in vitro SPF of 18 is determined by means of an Optometrics SPF-290 analyser (2 μl/cm² on Transpore film).

EXAMPLE 5

Preparation of a W/O Emulsion

| INCI Name | % w/w |
|---|---|
| PEG-30 dipolyhydroxy-stearate | 3.50 |
| PEG-22/dodecyl glycol copolymer | 1.50 |
| microcrystalline wax | 1.00 |
| hydrogenated castor oil | 1.00 |
| magnesium stearate | 1.00 |
| octyl stearate | 15.00 |
| coco glycerides | 2.00 |
| mineral oil | 3.00 |
| phenoxyethanols and (methyl, ethyl, propyl, butyl)parabens | 1.00 |
| octyl methoxycinnamate | 5.00 |
| dimethicone | 0.10 |
| deionised water | 51.90 |
| allantoin | 0.10 |
| magnesium sulfate | 1.00 |
| compound of formula (101) | 3.00 |
| propylene glycols | 4.00 |
| methylene bis-benzotriazolyl tetrametylbutylphenol (pH 5.5) | 6.00 |

The oil phase and the water phase are heated separately to 75–80° C. and are gently combined. This is followed by intense homogenisation and cooling to room temperature with slight stirring. With stirring, methylene bis-benzotriazolyl tetrametylbutylphenol is admixed to the emulsion so obtained.

The Australian standard for UVA protection (Australian/New Zealand Standard, 15/NZS 2604:1993) is met.

EXAMPLE 6

Preparation of a W/O Emulsion

| INCI Name | Formulation (A) % | Formulation (B) % |
|---|---|---|
| methoxy PEG-22/dodecyl glycol copolymer | 3.00 | 3.00 |
| PEG-22/dodecyl glycol copolymer | 3.00 | 3.00 |
| hydroxyoctacosanyl hydroxystearate | 3.00 | 3.00 |
| octyl stearate | 15.00 | 15.00 |
| coco glycerides | 2.00 | 2.00 |
| mineral oil | 3.00 | 3.00 |
| phenoxyethanols and (methyl, ethyl, propyl, butyl)parabens | 1.00 | 1.00 |
| octyl methoxycinnamate | 5.00 | 5.00 |
| dimethicone | 0.20 | 0.10 |
| water | 47.70 | 46.30 |
| allantoin | 0.10 | 0.10 |
| compound of formula (101) | 4.00 | 1.5 |
| magnesium sulfate | 1.00 | 1.00 |
| propylene glycols | 4.00 | 4.00 |
| methylene bis-benzotriazolyl tetrametyl-butylphenol (pH 5.5) (50% suspension) | 8.00 | 12.00 |

The oil phase and the water phase are heated separately to 75–80° C. and gently combined. This is followed by intense homogenisation and cooling to room temperature with slight stirring. With stirring, methylene bis-benzotriazolyl tetrametylbutylphenol is admixed to the emulsion so obtained.

In vitro SPF values of 18 (A) and 22 (B) are determined by means of an Optometrics SPF-290 analyser (2 μl/cm² on Transpore film).

EXAMPLE 7

Preparation of a W/O Emulsion

| INCI Name | % |
|---|---|
| polyglyceryl-2 dipolyhydroxystearate | 2.00 |
| PEG-30 dipolyhydroxystearate | 2.00 |
| hydroxyoctacoanyl hydroxystearate | 2.00 |
| zinc stearate | 1.00 |
| octyl stearate | 15.00 |
| coco glycerides | 2.00 |
| mineral oil | 3.00 |
| phenoxyethanols and (methyl, ethyl, propyl, butyl)parabens | 1.00 |
| bis-octylphenol methoxyphenyl triazine | 3.00 |
| octyl methoxycinnamate | 7.00 |
| dimethicone | 0.20 |
|  | 3.00 |
| deionised water | 53.70 |
| allantoin | 0.10 |
| magnesium sulfate | 1.00 |
| propylene glycols | 4.00 |

The oil phase and the water phase are heated separately to 75–80° C. and are gently combined. This is followed by intense homogenisation and cooling to room temperature with slight stirring.

An in vitro SPF of 15 is determined by means of an Optometrics SPF-290 analyser (2 μl/cm² on Transpore film).

What is claimed is:

1. A diphenyl compound of the formula

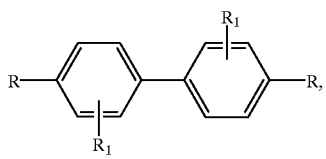 (1)

wherein

R is a camphor or hydantoin radical of the formulae

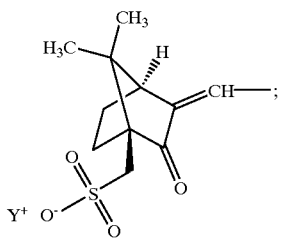 (1a)

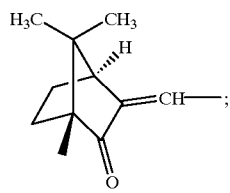 (1b)

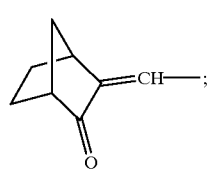 (1c)

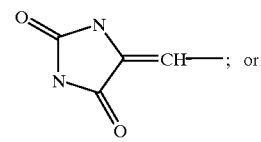 (1d)

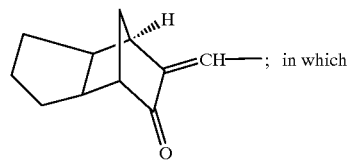 (1e)

in which $Y^+$ is hydrogen; an alkali metal or alkaline earth metal cation, ½ $Zn^{2+}$, ⅓ $Al^{3+}$, ½ $Ba^{2+}$,

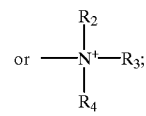

$R_2$, $R_3$ and $R_4$ are each independently of one another hydrogen; $C_1$–$C_5$alkyl or hydroxy-$C_1$–$C_5$alkyl; and $R_1$ is hydrogen; or $C_1$–$C_5$alkyl.

2. A diphenyl compound according to claim 1, which corresponds to the formula

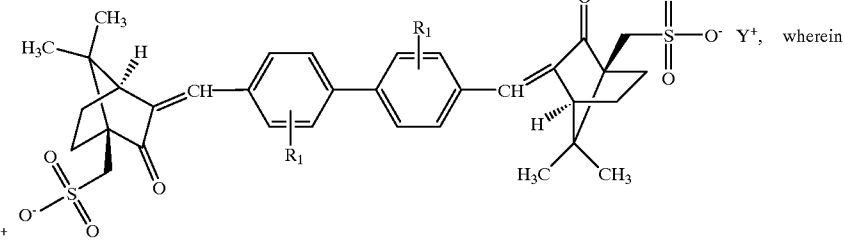 (2)

$R_1$ and $Y^+$ are as defined in claim 1.

3. A process for the preparation of the compound of formula (1) according to claim 1, which comprises reacting a diphenylbisaldehyde of the formula

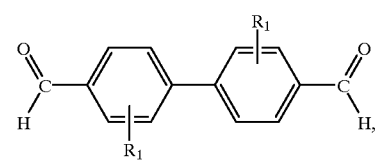 (3)

wherein

R₁ is as defined in claim 1, in the presence of a base or a Lewis acid with a corresponding camphor or hydantoin compound.

4. A method of protecting human and animal hair and skin from the harmful effect of UV radiation, which comprises applying thereto an effective protective amount of a compound of formula (1) according to claim 1.

5. A cosmetic formulation, which comprises a compound of formula (1) according to claim 1 together with a cosmetically tolerable carrier or auxiliary.

6. A formulation according to claim 4, which additionally comprises other UV protectives.

7. A formulation according to claim 6, wherein the additional other UV protectives are triazines, oxanilides, triazoles, vinyl group-containing amides or cinnamic acid amides.

* * * * *